(12) United States Patent
Unger

(10) Patent No.: US 7,210,312 B2
(45) Date of Patent: May 1, 2007

(54) ENERGY EFFICIENT, INEXPENSIVE EXTRACTION OF OXYGEN FROM AMBIENT AIR FOR PORTABLE AND HOME USE

(75) Inventor: Reuven Z-M Unger, Athens, OH (US)

(73) Assignee: Sunpower, Inc., Athens, OH (US)

( * ) Notice: Subject to any disclaimer, the term of this patent is extended or adjusted under 35 U.S.C. 154(b) by 259 days.

(21) Appl. No.: 10/910,401

(22) Filed: Aug. 3, 2004

(65) Prior Publication Data

US 2006/0026988 A1 Feb. 9, 2006

(51) Int. Cl.
*F25J 3/00* (2006.01)
*F25D 21/14* (2006.01)

(52) U.S. Cl. .............................. 62/640; 62/643; 62/285
(58) Field of Classification Search ................. 62/640, 62/643, 45.1, 285
See application file for complete search history.

(56) References Cited

U.S. PATENT DOCUMENTS

| | | | |
|---|---|---|---|
| 4,531,371 A | 7/1985 | Voronin et al. | |
| 4,666,480 A | 5/1987 | Mann | |
| 4,668,260 A | 5/1987 | Yoshino | |
| 4,698,079 A | 10/1987 | Yoshino | |
| 4,853,015 A | 8/1989 | Yoshino | |
| 5,148,680 A | 9/1992 | Dray | |
| 5,207,065 A | 5/1993 | Lavin et al. | |
| 5,305,610 A | 4/1994 | Bennett et al. | |
| 5,323,616 A | 6/1994 | Chretien et al. | |
| 5,410,885 A | 5/1995 | Smolarek et al. | |
| 5,590,543 A | 1/1997 | Agrawal et al. | |
| 5,592,832 A | 1/1997 | Herron et al. | |
| 5,644,932 A | 7/1997 | Dunbobbin et al. | |
| 5,694,790 A | 12/1997 | Lavin | |
| 5,704,227 A | 1/1998 | Krabbendam | |
| 5,730,003 A | 3/1998 | Nguyen et al. | |
| 5,893,275 A | 4/1999 | Henry | |
| 5,987,917 A | 11/1999 | Dannöhl | |
| 5,996,373 A | 12/1999 | Greter et al. | |
| 6,044,902 A | 4/2000 | Pahade et al. | |
| 6,212,904 B1 | 4/2001 | Arkharov et al. | |
| 6,279,345 B1 | 8/2001 | Arman et al. | |
| 6,357,259 B1 | 3/2002 | Higginbotham et al. | |
| 6,383,257 B1 | 5/2002 | McDermott et al. | |
| 6,477,859 B2 | 11/2002 | Wong et al. | |
| 6,681,764 B1 * | 1/2004 | Honkonen et al. | ..... 128/201.21 |
| 2004/0045315 A1 * | 3/2004 | Kamoshita et al. | ........... 62/615 |
| 2005/0274142 A1 * | 12/2005 | Corey | ........................ 62/643 |

* cited by examiner

*Primary Examiner*—William C. Doerrler
(74) *Attorney, Agent, or Firm*—Frank H. Foster; Kremblas, Foster, Phillips & Pollick

(57) ABSTRACT

Apparatus and method for separating oxygen directly from air, operating at substantially atmospheric pressure and recuperating energy used for cooling incoming air. An ambient air input leads from the atmosphere to a vessel for confining gases. A cryocooler has a cooled surface in the vessel for directly condensing oxygen from the air at substantially atmospheric pressure. The cryocooler cools the cold surface to a temperature greater than the boiling point temperature of nitrogen and not greater than the boiling point temperature of oxygen for condensing oxygen. A liquid/gas separator separates the liquid oxygen from residual gases which both flow out through separate outputs. Air is propelled through the system at substantially atmospheric pressure by an air impeller. A heat exchanger recovers cooling energy and dehumidifies incoming air by transferring heat from the incoming air to outgoing gases.

16 Claims, 2 Drawing Sheets

ENERGY EFFICIENT, INEXPENSIVE EXTRACTION OF OXYGEN FROM AMBIENT AIR FOR PORTABLE AND HOME USE

BACKGROUND OF THE INVENTION

1. Field of the Invention

This invention relates generally to separation of the gases in air and more particularly relates to an apparatus and method for extracting oxygen from ambient air to provide an inexpensive, portable, personal, oxygen source.

2. Description of the Related Art

Many individuals require or benefit from an oxygen rich source to improve their respiration. Such oxygen is conventionally supplied to a patient from a high pressure tank of compressed oxygen. The oxygen is filled into the tank by a large scale commercial operation that separates oxygen from air, compresses the oxygen and fills the tanks. The tanks are then distributed through a distribution system to individual patients. When the tanks are emptied, they are returned and refilled.

Prior art methods of oxygen separation include the use of a turboexpander and liquefaction by contacting the ambient air against a sufficiently cold surface that one or more component gases in the air are condensed. Often the components of air are liquefied and separated for sale as individual gases, although liquid nitrogen has also been used to condense the oxygen in air. Liquefaction in the prior art typically expends significant cooling energy to accomplish the liquefaction. After accomplishing the liquefaction, the remaining energy is put to no further use but is lost because it is carried away in the separated components and/or lost in a compression operation.

Although conventional oxygen separation and distribution systems have been of great benefit to patients who need oxygen, it has several disadvantages which add to the cost of the oxygen and make transporting the oxygen source difficult. Compression of the incoming air to at least 1 bar above atmospheric pressure is needed by prior art systems to accomplish conventional separation and movement of fluids through the system. The recovered oxygen also must be highly compressed so that the total mass of oxygen contained in the tanks is large enough to apportion the transportation cost for the heavy tanks over a larger mass of oxygen and therefore reduce the per unit cost of transportation and distribution.

Compression is typically accomplished at one or both of two stages of the separation process. Incoming air is compressed prior to separation not only to generate a pressure differential across the separator which is necessary to propel the air and its separated components through the separation system but also to provide adequate separation efficiency or rate of production. Furthermore, after separation, the separated components are often further compressed for filling into tanks. However, compressors are not only noisy and of significant weight, but also they are costly and consume significant energy, especially when designed to provide uncontaminated gases suitable for human respiration, and therefore add to the energy cost for producing oxygen. That energy is then lost when the oxygen is returned to substantially atmospheric pressure so it can be administered to a patient. Additionally, the need to transport heavy tanks adds a transportation cost to the oxygen in addition to the inconvenience of handling the tanks for suppliers, the patients and any care givers.

This conventional oxygen supply system has continued for decades because the separation and compression of oxygen in accordance with prior art techniques could be more efficiently and therefore less expensively accomplished by large scale, mass production systems devoted to the separation of the components of air for resale as compressed or liquid single components at various purity levels. The scaling down of the conventional separation systems for individual home use is impractical and would be prohibitively expensive.

For example, U.S. Pat. No. 5,893,275 describes a system as intended for home use. However, it requires a multiplicity of stages including a compressor, a first stage separator using an adsorptive process, a membrane separator or an ionic conduction system, and a liquefier which liquefies but does not separate the gases by liquefaction. U.S. Pat. No. 5,704,227 illustrates the use of a liquid nitrogen coolant as a cooling medium for condensing a volatile compound, such as a lower aldehyde, a glycol compound and water, from a gas such as nitrogen. Although a heat exchanger is used to pre-cool incoming gas, this system requires a liquid nitrogen source which makes such a system impractical for home use.

There is, therefore, a need for an oxygen separation system that can be economically implemented on a small scale so it will be practical for home use and is sufficiently small in size and weight that it can be made portable.

It is an object and feature of the present invention to provide an oxygen separation system which requires no compression and therefore can operate more energy efficiently by eliminating both the need to compress the incoming air prior to separation and by eliminating the need for compression of the oxygen for storage in tanks.

Another object and feature of the invention is to provide an oxygen separation system which separates the oxygen from air by direct liquefaction of only the oxygen.

Another object and feature of the invention is to provide an oxygen separation system using liquefaction but which recovers the cooling energy by using it in the liquefaction process and, as a result of recovering and using the energy, reduces the energy costs and permits use of simpler components which require less energy input.

BRIEF SUMMARY OF THE INVENTION

The invention directly condenses and separates oxygen from air at a low, preferably substantially atmospheric, pressure by cooling a surface within a confinement vessel to a temperature greater than the boiling point temperature of nitrogen and not greater than the boiling point temperature of oxygen. Air is impelled from the atmosphere into the vessel and against the cooled surface. Oxygen droplets condensed on the surface, fall and are collected by a liquid/gas separator and the oxygen and residual gases in the vessel are exhausted along separate paths and emitted from the system at atmospheric pressure. Incoming air is pre-cooled and water in the incoming air is condensed by effecting a transfer of heat from incoming air to the separated gases flowing outwardly from the vessel.

To accomplish this, an ambient air input, including an ambient air inlet passage, leads from the atmosphere to a confinement vessel. A cryocooler has its cooled surface positioned in the vessel for directly condensing oxygen from the air in the vessel. A cryocooler temperature control system causes the cold surface to be cooled to a temperature greater than the boiling point temperature of nitrogen and not greater than the boiling point temperature of oxygen so that only oxygen is condensed on the cooled surface. A liquid/gas separator connected to the vessel receives liquid oxygen drained from the cooled surface and separates the liquid oxygen from residual gases remaining in the vessel. An oxygen output, including an oxygen outlet passage, is connected to the liquid output of the separator for directing oxygen away from the vessel. A residual gases output, including a residual gas outlet passage, is connected to the gas output from the separator for exhausting residual gases from the vessel at substantially atmospheric pressure. An air impeller is used only to propel air and the separated gases through the system at a flow rate that is sufficient to separate out a useful quantity of oxygen. Because the system is open to the atmosphere, the impeller needs only to develop a pressure slightly above atmospheric pressure. The impeller moves the gases thorough the ambient air inlet passage, the residual gas passage and the vessel. A heat exchanger is connected to the input and outputs for transferring heat from incoming air to outgoing gases.

Figure 1:
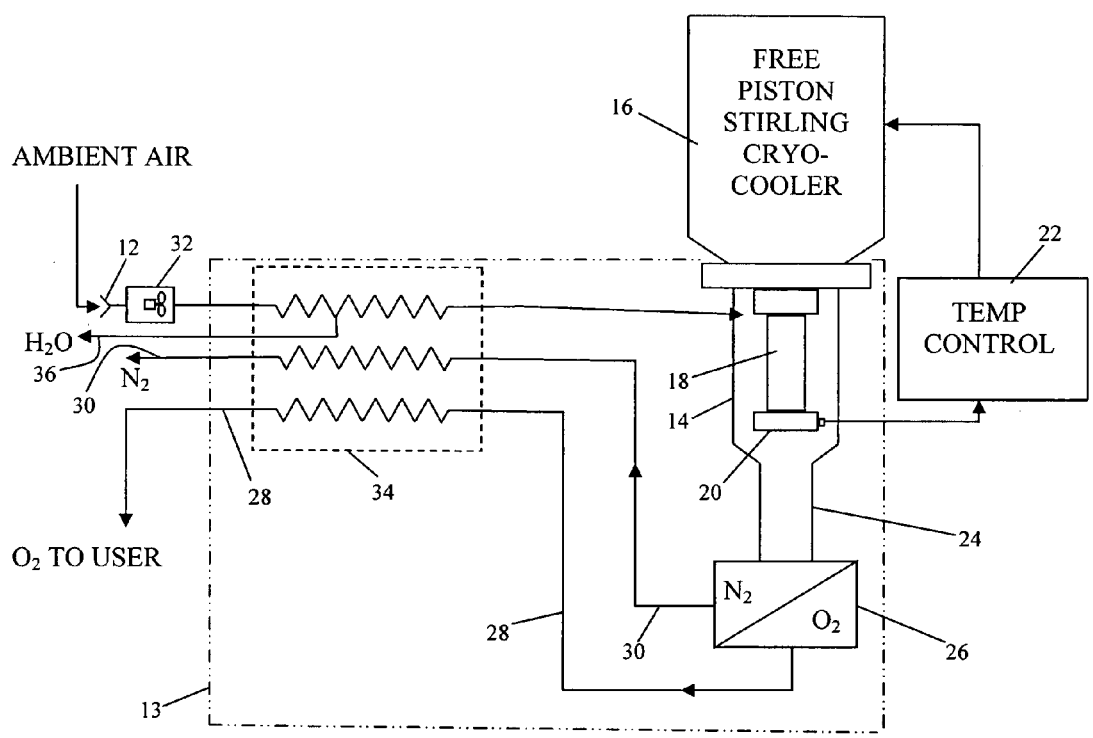
FIG. 1 is a schematic diagram of a basic embodiment of the invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

FIG. 1 is a schematic diagram of an embodiment of the invention illustrating its basic principles. The invention separates oxygen from air in a process that operates entirely at essentially atmospheric pressure because it uses no compressor. The invention outputs a mixture of the ordinary gas components found in air but the mixture is oxygen enriched, that is the proportion of oxygen is substantially greater than the proportion found in air entering the system. The enriched oxygen mixture is supplied at atmospheric pressure ready for use.

Referring to FIG. 1, an ambient air input 10 includes an ambient air inlet passage leading from an opening 12 for inputting atmosphere air, through an insulating enclosure 13, to a vessel 14 for confining gases. A free piston Stirling cryocooler 16, of a type well known in the art, has its cold finger 18 extending into the vessel 14 to provide a cooled surface 20. Oxygen in air that is incoming through the air input 10 is directly condensed on this cooled surface 20.

The cryocooler 16 has a conventional temperature control system for maintaining the cold surface at a temperature greater than the boiling point temperature of nitrogen, which is 77° K. at standard atmospheric pressure, and not greater than the boiling point temperature of oxygen, which is 90.1° K. at standard atmospheric pressure. A Stirling cryocooler allows the extraction of meaningful amounts of oxygen from a small scale and portable appliance.

The confinement vessel 14 includes a lower portion 24 for directing liquid oxygen, that drips from the cooled surface 20 by gravity, into a liquid/gas separator 26. The liquid/gas separator 26 may be of a type known in the art and is connected to the vessel 14 to receive liquid oxygen drained from the cooled surface 20 and separates the liquid oxygen from residual gases that remain in the vessel 14 after oxygen condensation. A suitable separator is the conventional trap-type of separator in which liquid flows by gravity into a receptacle which has an opening at or near its bottom followed by a trap in which the liquid collects and blocks passage of gas through the trap. Consequently, when the trap is filled, the liquid is a barrier to gas so only liquid can pass through the trap. The separator can be integrated with the vessel and liquid output can be directly from the vessel. The volume flow rate of air into the system and the rate of condensation should be maintained sufficient to keep the trap filled with liquid oxygen to assure that it remains a barrier to gas.

An oxygen output 28 includes an oxygen outlet passage and is connected to the liquid output of the separator 26 for directing oxygen away from the vessel 14 to the user. Similarly, a residual gases output 30, including a residual gas outlet passage, is connected to the gas output of the separator 26 for exhausting residual gases from the vessel at substantially atmospheric pressure.

Incoming air and the separated gases must be moved through the system at a flow rate that is sufficient to condense a useful quantity of oxygen. As oxygen is condensed on the cooled surface 20, fresh oxygen must be supplied into the vessel to replenish the condensed oxygen. For this purpose, an air impeller 32 driven by an electric motor is provided in the ambient air input 10. An air impeller is needed in the system to move the gases through the system at a useful flow rate and therefore need only create a pressure gradient through the system that is sufficient to overcome the flow resistance of the system and provide the desired flow rate. Although the impeller can be located elsewhere in the gas flow circuit of the system, it is preferably located in the input 10 and outside of the insulating enclosure 13. Because the impeller propels the gases through a series of open passages and enclosed spaces without any small orifices or closed valves, the air is propelled at substantially atmospheric pressure thorough the ambient air inlet passage, the residual gas passage and the vessel.

A critically important feature of the invention is the inclusion of a heat exchanger 34 because it is the principal means for recuperating energy used to condense the oxygen. Because both the oxygen flowing from the separator 26 through the oxygen output 28 and the residual gases flowing from the separator 26 through the residual gas output 30 have been cooled to temperatures far below the temperature of the ambient air, the cooling energy in these exiting gases can be used to pre-cool the air that is propelled through the ambient air input 10 into the vessel 14. For this purpose, the heat exchanger 34 is preferably a counter-flow heat exchanger having three passages separated by gas impervious, thermally conductive walls. The three heat exchanger passages are connected respectively in the ambient air input 10, the oxygen output 28 and the residual gas output 30. This permits heat to be transferred from the incoming ambient air to both the outgoing oxygen and the outgoing residual gases. This pre-cooling and energy transfer serves not only to reduce the energy required at the cooling surface 20 to condense the oxygen, but also warms the outgoing oxygen and residual gases to near the ambient temperature. This makes the system safer and provides oxygen to the user at a temperature which is safer and more comfortable for consumption by a user.

The use of a counter-flow heat exchanger arrangement, in which the heat rejecting gas flows in one direction and the heat absorbing gases flow in the opposite direction, provides the most efficient heat transfer. However, although counter-flow is very much preferred because of its greater efficiency, it is not necessary. Similarly, the heat exchanger can have only two passages to recover heat from only one of the outgoing gases, most effectively the residual gases, but this reduces the energy recovery efficiency advantages of the invention.

Cold Finger Temperature Control. Because Stirling cryocoolers and control systems for controlling their cold finger temperature are known in the art, they are not described in detail. The controls systems typically include a cold finger temperature sensor connected in a feedback control system that controls the cooling energy delivered by the cryocooler to maintain it at a set point temperature. Since the boiling point temperature at standard pressure for $O_2$ is 90.1° K. and for $N_2$ is 77° K., the cooled surface 20 must be cooled down to at least 90.1° K. at standard pressure so oxygen will condense but should not be cooled down as low as 77° K. so that nitrogen will not condense. Preferably, the cooled surface 20 is cooled to just below 90.1° K., such as to 87° K. This is cool enough to condense the oxygen but well above the boiling point temperature of nitrogen in order to avoid energy loss from excessive and unnecessary cooling. Thus, the invention has improved energy efficiency because the cooled surface does not need to be cooler to condense other constituents of the air.

Because boiling point temperatures change with a change in pressure, these temperatures, and particularly the set point temperature of the control system, will be changed correspondingly for other ambient pressures, for example when an embodiment of the invention is operated at higher elevations. Similarly, because a pressure gradient must be developed across the system in order to move gases through the system, the temperature control system set point temperature can be adjusted to compensate for the small variation within the system from the ambient pressure.

Air Impeller Parameters. Embodiments of the invention can operate essentially at atmospheric pressure in comparison to prior art systems because there are no compressors, valves or orifices to maintain a higher pressure. The system is open to the atmosphere. Therefore, the air impeller must only develop a sufficiently large pressure gradient across it to overcome the pressure drop in the passages and along the gas flow path, parasitic losses and to obtain the volume flow rate needed to supply sufficient oxygen to a user. The pressure gradient across the impeller is then dropped across the system so that the gases leaving the system are at atmospheric pressure. Since most humans consume 2–3 liters of air per minute and air contains about 20% oxygen, the system would require a flow rate of approximately 10–15 liters of air per minute if the system were 100% efficient and supplied pure oxygen.

However, the system is not 100% efficient and it is believed that a flow rate on the order of 50 liters per minute would be more than sufficient and preferred. Furthermore, a lower oxygen separation efficiency is tolerable because a higher flow rate will compensate for inefficiency and does not incur any significant additional cost because compression of the incoming air is not required.

Of course the pressure gradient required of the impeller is a function of passage diameters and other physical properties of the flow path that affect the fluid flow. However, unlike the prior art, the invention requires an impeller pressure gradient below 1 bar and is capable of operating most effectively with a pressure gradient far below 1 bar.

Initial calculations indicate that the impeller would require less than 1 psi and more realistically should develop a pressure on the order of 0.33 psi above the ambient atmospheric pressure in order to obtain the flow rates described above. Thus, the invention operates at substantially atmospheric pressure. At no stage along the process of conversion of the oxygen from the ambient atmosphere to delivery of the oxygen rich supply to the user is any gas in the system pressurized beyond substantially atmospheric pressure.

Initial calculated estimates of power consumption by embodiments of the invention indicate that power consumption by the impeller motor will be on the order of 5 watts and the cryocooler would consume on the order of 160 to 200 watts. Therefore, energy consumption by embodiments of the invention is very small.

Water Removal. Because atmospheric air entering the system is pre-cooled in the heat exchanger 34, atmospheric moisture will condense in the heat exchanger 34. Water removal from the incoming air is important, including the location in the system where it is removed. The water should be extracted and separated from the incoming air before the incoming air reaches the vessel 14. This avoids freezing and clogging of the system flow passages with ice and avoids the buildup of deposits of frozen water on the cooled surface 20. The removal of the water is illustrated diagrammatically in FIG. 1 by a water drain pipe 36 for transporting water from the system.

The water extracted from the incoming air can be simply drained away. Preferably, however, energy can also be recovered from the cold water by circulating the cold water through a heat exchanger positioned upstream of the principal heat exchange 34 to provide a preliminary pre-cooling of the incoming air. In addition or in the alternative, the water can be used to humidify the outgoing oxygen. After or instead of either or both of these uses, the water can be disposed of by feeding it back into the outgoing residual gas stream. Feeding the water back into the residual gas stream has the advantage that there will be a greater flow volume because air is 80% nitrogen and therefore the water can be evaporated into the outgoing residual gas stream and returned to the atmosphere. Feeding at least a portion of the water back into the oxygen stream provides the advantage that it re-humidifies the oxygen making is less likely to dry out the tissues of the user.

Figure 2:
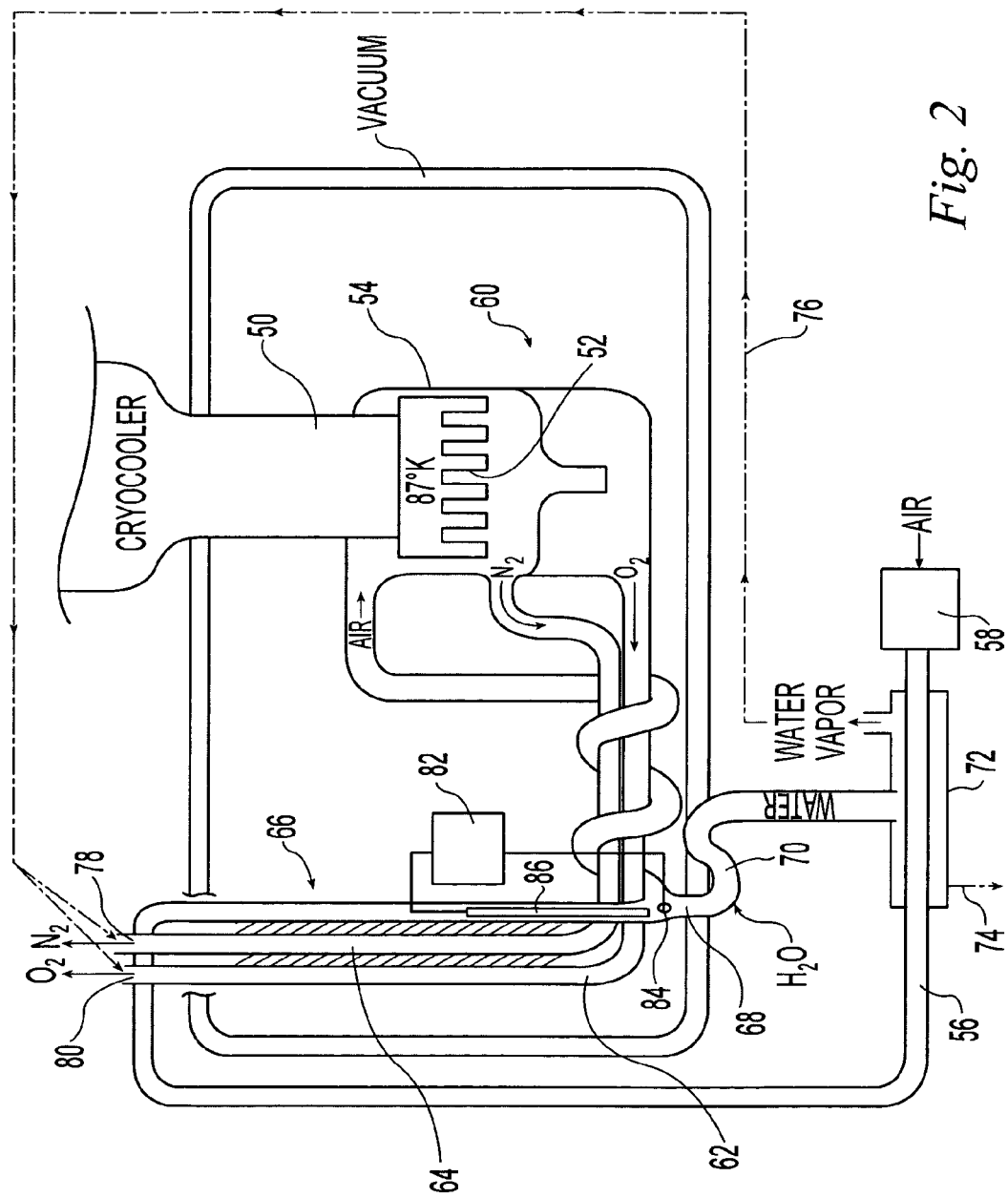
FIG. 2 is a schematic diagram of an alternative embodiment of the invention.

FIG. 2 illustrates an alternative embodiment with the addition of these and other features. As in the embodiment of FIG. 1, a cryocooler cold finger 50 extends into a vessel 54 and has a cooled surface 52. Incoming air is forced through an air input passage 56 by an impeller 58 and into the vessel 54. Oxygen condenses on the cooled surface 52 and drips into the air/liquid separator 60 and then flows out through the oxygen output passage 62. The oxygen is forced along its flow path by the pressure of the incoming air and its vapor pressure as it vaporizes along its output path. The residual gases in the vessel 54 are forced by the pressure of the incoming air out through the residual gas output passage 64.

Water condensing in the portion of the ambient air input passage 56 that extends through the heat exchanger 66 flows by gravity down through a liquid/gas separator comprising a water outlet 68 and a gas trap 70 and then flows into a water jacket 72, or other heat exchanger, that is in thermal conductive connection to the ambient air input passage 56. This water preliminarily pre-cools the incoming ambient air. Other heat exchanger configuration can utilize other water draining configurations. The water should exit through an outlet in or below the heat exchanger where the temperature is optimal for collection and drainage of the water.

Water collected in the water jacket 72 can be used or disposed of in one or more of a variety of ways as described above. Some or all of the water in the water jacket 72 can be drained through a drain outlet 74. Water or water vapor can be directed or pumped through a passage or conduit 76 to the outlet end 78 of the residual gas output passage 64 and/or to the outlet end 80 of the oxygen output passage 62. This can be accomplished by using the apparatus and methods known in the art for humidifying a gas, such as passing the gas over a pan of the water or through a water-soaked, fibrous matrix similar to a filter. Alternatively, the water from the water jacket 72 can be directly evaporated to the atmosphere.

In view of the low temperatures at which the oxygen and residual gases enter the heat exchanger 66 (or heat exchanger 34 in FIG. 1), the water condensed in the ambient air input passage 56 may freeze in or near that heat exchanger, accumulate ice and block the passage. To prevent this, the temperature of the output passage in this vicinity can be controlled by one or more of: (1) adjustment of the cooling energy supplied by the Stirling cryocooler; (2) a dedicated heater using a temperature sensor and a temperature control system; and (3) using heat rejected from the Stirling cryocooler. FIG. 2 illustrates a temperature control 82 having a temperature input sensor 84 and connected to control a heater 86, such as an electrically heated resistive strip. The control has a set point temperature slightly above the freezing temperature of water to assure that no water can freeze in the ambient air input passage 56. However, as illustrated in FIG. 1, the water drain outlet may be located at an intermediate position along the flow path within the heat exchanger. Because there will be a temperature gradient from one end of the heat exchanger to the opposite end, the temperature along the flow path through the heat exchanger can be measured and the drain located where the temperature is slightly above the freezing temperature of water under normal, steady state operation of an embodiment of the invention. As a consequence, not much heat energy will need to be applied to prevent freezing of the water.

Operation. Embodiments of the invention operate by cooling a surface within a confinement vessel to a temperature greater than the boiling point temperature of nitrogen and not greater than the boiling point temperature of oxygen. Air is impelled from the atmosphere into the vessel, against the cooled surface and the air components are impelled out of the vessel, all at substantially atmospheric pressure. Oxygen droplets that condense on and drop from the cooled surface are separated from the residual gases in the vessel. The incoming air is cooled and water is condensed from it by transferring heat from the incoming air to the gases flowing outwardly from the vessel.

Because the cooled surface is the lowest temperature in the system, oxygen begins to vaporize soon after it passes through the separator. Therefore, oxygen in the oxygen output passage will evaporate and expand as it warms and this expansion will cause gaseous oxygen to flow out. The residual gases will be composed principally of nitrogen and will be forced out by the pressure of the incoming air. Consequently, all components of the air are returned to, and exit the system in, a gaseous state.

The departing oxygen will be oxygen rich but not pure oxygen. Some oxygen would still be in the departing residual gases, mostly nitrogen, along with the other constituent gases in air. Furthermore, some nitrogen and other constituent gases will be mixed with the oxygen. It is not necessary that the trap of the liquid/gas separator always be filled to provide a barrier to the residual gases. The purpose of the invention is not to provide pure oxygen but rather is to provide an oxygen rich mixture that can be consumed by humans. Because energy is not wasted on compression of any gases, it is not necessary that even a high proportion of the oxygen be condensed.

In order to allow the liquid oxygen an opportunity to evaporate and to prevent liquid oxygen from flowing out of the system, the oxygen output passage desirably has an adequate combination of length and rise above the liquid level in the separator. This can be determined from experimentation and the knowledge of a person of ordinary skill in the art. As an alternative, the liquid oxygen can be drained into tanks for storage.

Advantages. The advantages of the present invention arise from the combination of separation of oxygen by condensation upon a cooled surface, operating it at substantially atmospheric pressure and recovering the energy from the outgoing constituents of air that entered the system. The use of a Stirling cryocooler is particularly advantageous because they are small, lightweight and energy efficient.

The most significant advantage of the invention is its small scale. The invention neither has nor requires a compressor or concentrator unlike the prior art which requires a compressor or concentrator before separation as a means of moving the gases through the prior art process. The invention has no evaporator or expansion valve and does not use an expensive separator such as a membrane separator. The prior art systems for oxygen separation are generally associated with large scale commercial systems intended to separate components of air for resale as compressed or liquid single component gases of various purity levels. The liquefying means for these large scale systems is generally a turboexpander. Stirling coolers are not used for these prior art systems because they do not scale to sizes that would support a commercial gas sales operation.

Embodiments of the invention are small enough to be portable. The portability can be on two levels. The first level is that the unit is small enough to move around from place to place but still rely on an electrical wall outlet for input power. Prior art units which are intended for personal use still require a compressor or concentrator and such devices add a very significant weight to the unit. Prior art personal oxygen supplies require a tank which heavy and difficult to transport by an individual. The second level of portability is true portability, whereby the oxygen extractor is powered by a battery, and so is fully mobile and capable of being carried by a person while being used and eliminates the need to carry a tank.

A very small pressure is required to propel the air and gases through embodiments of the invention. The invention requires only a sufficient flow of air to keep a fresh supply of air entering the system to attain the desired rate of oxygen production. For this, a small fan is all that is needed for the impeller. Of course other low pressure, high volume air impelling devices can be used, such as a bellows or diaphragm type of pump.

Embodiments of the invention can operate at low atmospheric pressure, such as occur at high elevations, because of the temperature control. The temperature control is simply adjusted to compensate for the change in the boiling point temperatures that result from changes in ambient atmospheric pressure.

The heat exchanger allows the heat of incoming air to be extracted by outgoing, cold, separated air constituents. The invention recuperates very nearly all the heat extracted from the air in the separation process. The prior art discards energy in the form of retaining the desired gas in liquid form or releasing unwanted portions of the input gas(es) to the atmosphere in a cold state, without recuperating the heat removed. Although counter flow heat exchangers are known in the prior art in other machines, the counter-flow heat exchanger is a very important component of the present invention. Here, ideally the gases leaving the system, both $O_2$ and $N_2$ (along with other constituents of air), would be at room temperature so all the heat entering the system in the incoming air would be removed by the exiting gases, i.e. they cool (or "pre-cool") the incoming air. Therefore, the cooling required by the cryocooler is minimized and limited to removing heat from inefficiencies such as radiation and conduction through surrounding insulation, the inefficiency of the recovery of the thermal energy, the work to push gas through system, and losses in the cryocooler.

While certain preferred embodiments of the present invention have been disclosed in detail, it is to be understood that various modifications may be adopted without departing from the spirit of the invention or scope of the following claims.

The invention claimed is:

1. An apparatus for separating oxygen from air and supplying the oxygen for use at atmospheric pressure, the apparatus comprising:
   (a) a vessel for confining gases;
   (b) an ambient air input including an ambient air inlet passage leading from the atmosphere to the vessel;
   (c) a cryocooler having a cooled surface in the vessel for directly condensing oxygen from the air, the cryocooler having a control system for cooling the cold surface to a temperature greater than the boiling point temperature of nitrogen and not greater than the boiling point temperature of oxygen for condensing oxygen from air in the vessel;
   (d) a liquid/gas separator connected to the vessel to receive liquid oxygen drained from the cooled surface and separate the liquid from residual gases remaining in the vessel;
   (e) an oxygen output including an oxygen outlet passage connected to a liquid output of the separator for directing oxygen away from the vessel;
   (f) a residual gases output including a residual gas outlet passage connected to a gas output from the separator for exhausting residual gases from the vessel at substantially atmospheric pressure;
   (g) an air impeller for propelling air through the ambient air inlet passage, the residual gas passage and the vessel, the impeller developing a pressure gradient of less than 1 bar;
   (h) a heat exchanger having at least two passages separated by a gas impervious, thermally conductive wall for conducting heat from gas in a first passage to gas in a second passage, the first heat exchanger passage being connected in the air input passage and the second passage being connected in the residual gas outlet passage for transferring heat from incoming air to outgoing residual gases; and
   (i) a water passage connected in communication with said first passage of the heat exchanger for draining water condensed in the ambient air inlet passage, the water passage being connected to the oxygen outlet passage for returning water to outgoing oxygen gas.

2. An apparatus in accordance with claim 1 and further comprising a liquid/gas separator in the ambient air input for separating from incoming air any water condensed from the air by heat transfer in the heat exchanger.

3. An apparatus in accordance with claim 1 wherein the heat exchanger further comprises a third passage separated from the first passage by a gas impervious, thermally conductive wall and separated from the second passage by an impervious wall, the third heat exchanger passage being connected in the oxygen output passage for conducting heat from incoming ambient air to outgoing oxygen.

4. An apparatus in accordance with claim 1 wherein the heat exchanger is connected as a counter flow heat exchanger.

5. An apparatus in accordance with claim 4 wherein the pressure gradient is less than 1 psi.

6. An apparatus in accordance with claim 5 wherein the pressure gradient does not exceed 0.33 psi.

7. An apparatus in accordance with claim 1, wherein a temperature sensor and a heater are connected to the water passage or the heat exchanger and are connected to a heater control system for maintaining the water temperature above the freezing temperature of water.

8. An apparatus in accordance with claim 1 wherein the cryocooler is a free piston Stirling cryocooler.

9. An apparatus in accordance with claim 1, wherein the cryocooler has a power rating of not more than 2 kilowatts.

10. A method for directly condensing and separating oxygen from air, the method comprising:
    (a) cooling a surface within a confinement vessel to a temperature greater than the boiling point temperature of nitrogen and not greater than the boiling point temperature of oxygen;
    (b) impelling gas from the atmosphere into the vessel, against the surface and out of the vessel, the impelled gas being at a pressure less than 1 bar above ambient atmospheric pressure;
    (c) collecting condensed oxygen droplets that fall from the cooled surface and separating the oxygen from gases in the vessel;
    (d) cooling incoming air and condensing water in the incoming air by effecting a transfer of heal from incoming air to uncondensed gases flowing outwardly from the vessel; and
    (e) cooling the incoming air by transferring heat from the incoming air to the condensed water before transferring heat to gases flowing outwardly from the vessel.

11. A method in accordance with claim 10 and further comprising: cooling incoming air and condensing water in the incoming air by also effecting a transfer of heat from incoming air to separated oxygen.

12. A method in accordance with claim 10 and further comprising: transferring heat absorbed from the cooling surface to gases exhausted from the confinement vessel.

13. A method in accordance with claim 10 and further comprising: evaporating the condensed water into oxygen exhausted from the vessel.

14. A method in accordance with claim 10 and further comprising: applying sufficient heat to the condensed water to prevent freezing of the water.

15. A method in accordance with claim 10 wherein the impelled gas is at a pressure below 1 psi.

16. A method in accordance with claim 10 wherein the impelled gas is at a pressure not more than 0.33 psi.

* * * * *